(12) United States Patent
Ein-Gal

(10) Patent No.: US 6,718,012 B2
(45) Date of Patent: Apr. 6, 2004

(54) ELECTROMAGNETIC WAVE ENERGY EMITTER

(76) Inventor: Moshe Ein-Gal, 30 Azar Street, Ramat Hasharon 47203 (IL)

( * ) Notice: Subject to any disclaimer, the term of this patent is extended or adjusted under 35 U.S.C. 154(b) by 96 days.

(21) Appl. No.: 10/157,396

(22) Filed: May 30, 2002

(65) Prior Publication Data

US 2003/0223545 A1 Dec. 4, 2003

(51) Int. Cl.[7] ............................................... H01J 35/00
(52) U.S. Cl. ........................................ 378/121; 378/136
(58) Field of Search .................. 378/119–124, 134–143

(56) References Cited

U.S. PATENT DOCUMENTS 5,729,583 A * 3/1998 Tang et al. ................. 378/122
6,148,061 A 11/2000 Shefer et al.

* cited by examiner

Primary Examiner—Craig E. Church
(74) Attorney, Agent, or Firm—David Klein; Dekel Patent Ltd.

(57) ABSTRACT

An electromagnetic wave energy emitter including a generally cylindrical probe including generally coaxial first and second electrodes, each of the electrodes having an at least partially cylindrical shape, one of the electrodes being energizable to emit electrons and the other of the electrodes being adapted to receive the electrons and generate electromagnetic wave energy. A grid element may be placed between the first and second electrodes. A controller may be in communication with the grid element, adapted to control a potential of the grid element. The grid element may have an at least partially cylindrical shape. The grid element may be placed concentrically or non-concentrically with respect to the first and second electrodes.

20 Claims, 2 Drawing Sheets

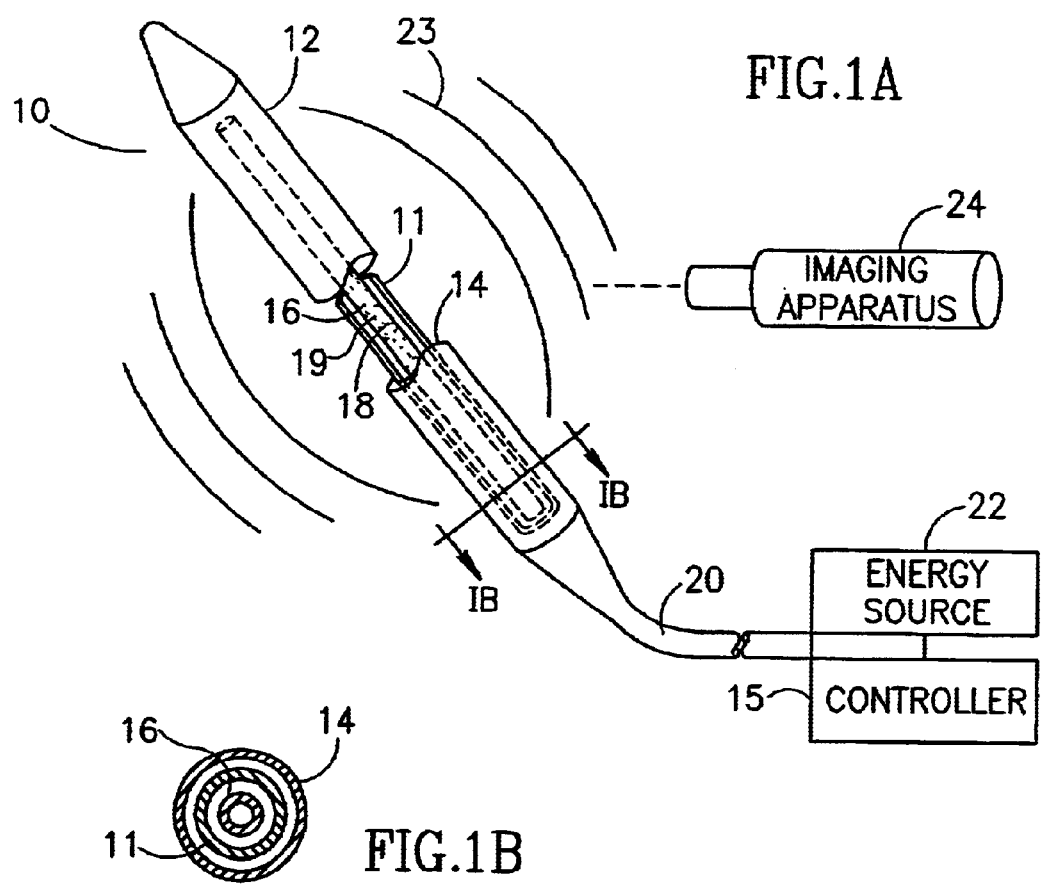
FIG.1A
FIG.1B
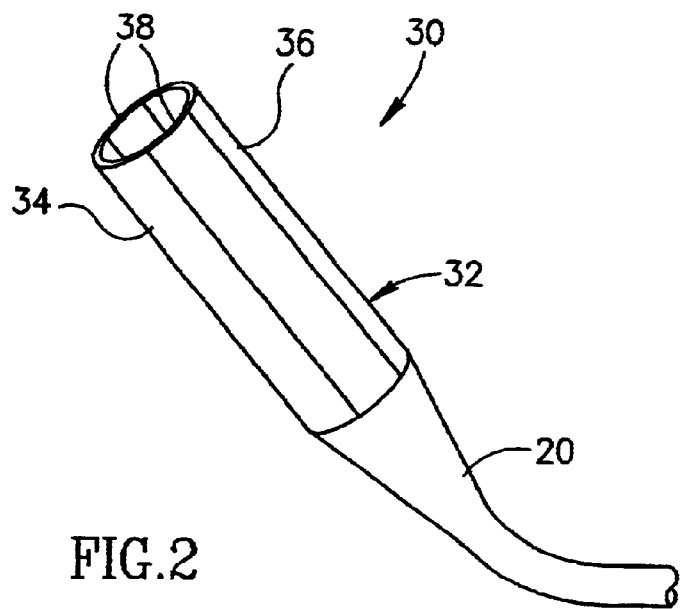
FIG.2

ELECTROMAGNETIC WAVE ENERGY EMITTER

FIELD OF THE INVENTION

The present invention relates generally to imaging and radiation treatment apparatus and particularly to such apparatus that employs nanostructures to generate electromagnetic wave energy, such as x-rays.

BACKGROUND OF THE INVENTION

X-ray imaging and treatment in-situ in body cavities or lumens are known. For example, miniature transducers are known that generate x-rays by direct conversion of laser light (e.g., femtosecond lasers) into x-ray radiation. The miniature transducers may be coupled to flexible insertion devices to permit in-situ radiation treatment within a human body. The flexible insertion device may include optical fibers and/or electrical conductors to supply electrical and/or optical signals to the miniature energy transducer. The miniature energy transducer may include a cathode structure and anode structure spaced apart within a transducer body; and the cathode, anode, and transducer body form a sealed cavity. Electrons may be accelerated from the cathode structure to the anode structure and are stopped by the anode to generate x-rays by the application of electrical pulses.

U.S. Pat. No. 6,148,061 to Shefer et al., issued Nov. 14, 2000, describes a miniature x-ray unit that may be insertable in a body lumen. The x-ray unit includes a first electrical node, a second electrical node and an insulating material. The first and second nodes are separated by a vacuum gap. The first node includes a base portion and a projecting portion, wherein the projecting portion and the second node are surrounded by an x-ray transmissive window through which x-rays exit the unit. The insulating material coaxially surrounds the base portion of the first node such that the insulating material is recessed from the vacuum gap, and the insulator does not extend into the vacuum gap. Recessing the insulating material from the vacuum gap may decrease the likelihood that the insulator will electrically break down due to the accumulation of electrical charge, and/or the accumulation of other materials on the surface of the insulator. On of the nodes is the anode and the other node is the cathode. The cathode is preferably a cold gated field emitter array (FEA) which provides an electron current having a magnitude that is sufficient to satisfy the time constraints on x-ray dose delivery. The cathode is located within a miniature vacuum (i.e., evacuated) chamber in close proximity to the anode, which is maintained at a voltage of up to about 50 kV. Electrons impinge on the anode in a geometry which may allow the emitted x-ray flux to escape from the anode through a transmissive x-ray window (e.g., cylindrically shaped) which surrounds the vacuum gap.

However, the U.S. Pat. No. 6,148,061 x-ray unit may have some disadvantages. For example, the source length is limited by the inter-electrode spacing and, therefore, the axial radiation distribution is non-uniform. Moreover, since the cathode is located within a miniature vacuum chamber, the size of the x-ray window and the amount of radiation that may pass therethrough are constrained to a small area near the nose of the x-ray unit.

SUMMARY OF THE INVENTION

The present invention seeks to provide an improved apparatus electromagnetic wave energy emitter (or transducer, the terms being used interchangeably throughout the specification and claims) that may be used for in-situ imaging and radiation treatment. In one embodiment of the invention, the emitter may be constructed as a slender probe with annular electrodes, such as one or more generally coaxial and cylindrical pairs of electrodes. One of the electrodes may serve as an anode and the other as a cathode. Each pair of electrodes may be individually energized. The energy may be emitted over a substantial portion of the length of the electrodes, thereby providing a significantly larger energy emission window not found in the prior art.

In one embodiment, the probe may be shaped as a slender needle. In another embodiment, there may be provided a plurality of such needles, which may be generally parallel to each other. In yet another embodiment, the probe and electrodes may have a helical construction for further increasing the possible treatment volume.

The probe may form part of an imaging system, which cooperates with an energy emission detector, such as but not limited to, a film, a scintillating screen, a fluoroscope or a detector array. In accordance with one embodiment of the present invention, the detector may comprise a linear coaxial array constructed as a needle (or helix), which may be inserted generally in parallel to the energy transducer.

The electromagnetic wave energy may be produced by a hot cathode. Alternatively, in accordance with a preferred embodiment of the invention, a cold cathode may be employed comprising nanostructures, such as but not limited to, carbon nanotubes and nanoparticles, which may produce a flux of electrons for generating electromagnetic wave energy, such as x-rays.

There is thus provided in accordance with a preferred embodiment of the present invention an electromagnetic wave energy emitter including a generally cylindrical probe including generally coaxial first and second electrodes, each of the electrodes having an at least partially cylindrical shape, one of the electrodes being energizable to emit electrons and the other of the electrodes being adapted to receive the electrons and generate electromagnetic wave energy. A grid element may be placed between the first and second electrodes. A controller may be in communication with the grid element, adapted to control a potential of the grid element. The grid element may have an at least partially cylindrical shape. The grid element may be placed concentrically or non-concentrically with respect to the first and second electrodes.

In accordance with a preferred embodiment of the present invention the first electrode includes a generally hollow cylindrical shell and the second electrode is disposed at least partially inside the first electrode.

Further in accordance with a preferred embodiment of the present invention the probe includes a generally hollow cylindrical shell, and the first and second electrodes are disposed and insulatingly spaced apart from one another on the shell.

Still further in accordance with a preferred embodiment of the present invention the first and second electrodes extend generally axially along a longitudinal length of the shell.

In accordance with a preferred embodiment of the present invention a flexible cable is in electrical connection with at least one of the first and second electrodes. In accordance with another preferred embodiment of the present invention the probe is shaped like a needle and may have a sharp nose and a relatively rigid extended or elongate body. Such an embodiment may be used as an x-ray needle.

Further in accordance with a preferred embodiment of the present invention an energy source is provided for energizing at least one of the first and second electrodes.

Still further in accordance with a preferred embodiment of the present invention imaging apparatus is provided that is adapted to form images of structures illuminated by electromagnetic wave energy generated by the emitter. One of the electrodes may serve as the cathode and the other may serve as the anode.

In accordance with a preferred embodiment of the present invention nanostructures are disposed on at least one of the first and second electrodes, the nanostructures being energizable to emit electrons. The nanostructures may include an electron emitting material, or an overcoating of at least one nanolayer of an electron emitting material.

Further in accordance with a preferred embodiment of the present invention the electron emitting material has a surface morphology that is sufficiently nanoscopically rough to provide multiple potential field emission sites.

Still further in accordance with a preferred embodiment of the present invention a plurality of the probes are generally parallel to one other.

In accordance with a preferred embodiment of the present invention the probe has a generally helical construction.

Further in accordance with a preferred embodiment of the present invention the imaging apparatus includes an energy emission detector.

Still further in accordance with a preferred embodiment of the present invention the energy emission detector includes at least one of a film, a scintillating screen, a fluoroscope and a detector array.

BRIEF DESCRIPTION OF THE DRAWINGS

The present invention will be understood and appreciated more fully from the following detailed description taken in conjunction with the drawings in which:

FIG. 1A is a simplified pictorial illustration of an electromagnetic wave energy emitter, constructed and operative in accordance with a preferred embodiment of the present invention;

FIG. 1B is a simplified cross-sectional illustration of a portion of the electromagnetic wave energy emitter of FIG. 1A, taken along lines 1B—1B in FIG. 1A;

FIG. 2 is a simplified pictorial illustration of an electromagnetic wave energy emitter, constructed and operative in accordance with another preferred embodiment of the present invention;

DETAILED DESCRIPTION OF THE PREFERRED EMBODIMENT

Figure 3:
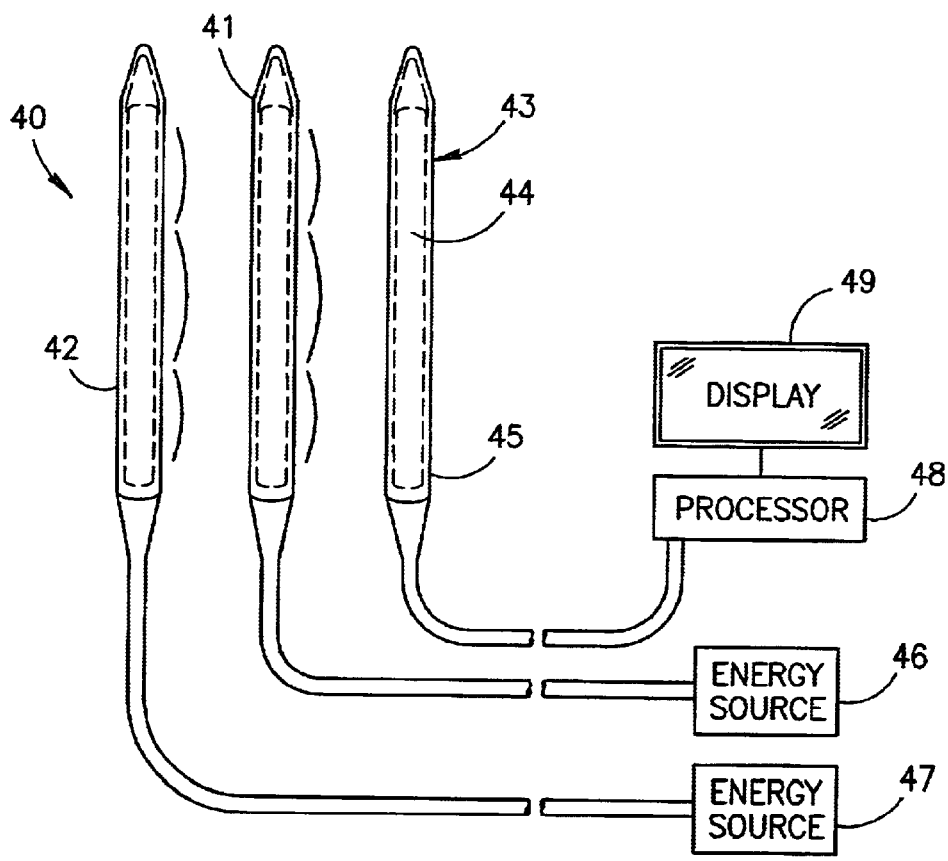
FIG. 3 is a simplified pictorial illustration of an electromagnetic wave energy emitter comprising multiple probes and an imaging system, constructed and operative in accordance with yet another preferred embodiment of the present invention.

Reference is now made to FIG. 1A, which illustrates an electromagnetic wave energy emitter 10, constructed and operative in accordance with a preferred embodiment of the present invention.

Transducer 10 may include a generally cylindrical probe 12 comprising first and second electrodes 14 and 16, respectively, forming an annular construction. First electrode 14 preferably comprises a generally hollow cylindrical shell and second electrode 16 is preferably disposed at least partially inside first electrode 14. First and second electrodes 14 and 16 preferably extend generally axially along a longitudinal length of the cylindrical shell. Second electrode 16 preferably serves as the cathode and may be energized to a high positive voltage, such as but not limited to, 20 kV. First electrode 14 preferably serves as the anode and may be grounded. There is preferably a vacuum in the space between the electrodes 14 and 16. In one embodiment of the invention, a grid element 11 may be placed between first and second electrodes 14 and 16, thereby forming a triode. Grid element 11 may be controlled by a controller 15. The potential of grid element 11 may be controlled by controller 15 to control the flow of electrons between second and first electrodes 16 and 14 (from cathode to anode). Grid element 11 may be placed concentrically or non-concentrically with respect to first and second electrodes 14 and 16, and may be partially or completely cylindrical in shape, for example (as may be seen best in FIG. 1B). Controller 15 may control other functions of electromagnetic wave energy emitter 10 as well.

Alternatively, the roles of first and second electrodes 14 and 16 may be reversed. Accordingly, first electrode 14 may serve as the cathode and may be grounded, and second electrode 16 may serve as the anode, energized to a substantial negative voltage, such as but not limited to, −20 kV.

A flexible cable 20 is preferably in electrical connection with one or both of first and second electrodes 14 and 16. Flexible cable 20 may be connected to an energy source 22, such as a high voltage source, for energizing either electrode and forming an electrical field to accelerate electron emission from the cathode to the anode.

The electromagnetic wave energy generated by either first or second electrode 14 or 16 may be generated by means of a hot cathode. Alternatively, in accordance with a preferred embodiment of the invention, a cold cathode may be employed, as is now described.

A preferred method of forming a cold cathode is by disposing nanostructures 18 on one or both of the first and second electrodes 14 and 16. The nanostructures 18 may comprise an electron emitting material 19. Alternatively, the nanostructures 18 may comprise nanostructures or microstructures conformally overcoated with one or more nanolayers of electron emitting material 19, the overcoated electron emitting material 19 being disposed on at least a portion of the substrate nanostructures or microstructures, preferably having a surface morphology that is sufficiently nanoscopically rough to provide multiple potential field emission sites per substrate nanostructure or microstructure. The roughness features may be in the range of 0.1 nm to 700 nm in any single dimension, although the invention is not limited to these values. The number of microstructures per unit area may be in the range of about $10^6$ to about $10^{12}$ microstructures per $cm^2$, although the invention is not limited to these values.

Suitable nanostructures or microstructures that may serve as a substrate for overcoating with one or more nanolayers of an electron emitting material comprise, without limitation, organic materials and inorganic materials, including, for example, glasses, ceramics (e.g., alumina or silica), metals (e.g., aluminum, cobalt, copper, molybdenum, nickel, platinum, tantalum, or combination thereof), and semiconductors (e.g., silicon). Preferred electron-emitting materials exhibit low electronic work functions, high thermal conductivity, high melting temperatures, negligible outgassing and tend to form nanoscopically rough coatings.

Suitable electron emitting materials comprise, without limitation, nickel or cobalt, for example.

The organic material from which the microstructures may be formed may be formed by a number of techniques, such as but not limited to, vapor phase deposition (e.g., vacuum evaporation, sublimation, and chemical vapor deposition), and solution coating or dispersion coating (e.g., dip coating, spray coating, spin coating, and blade or knife coating).

Electrodes 14 and 16 may be constructed of any suitable material that serves as a good base for the nanostructures 18, and which conducts electricity to the nanostructures 18 to energize them, thereby emitting electrons at the multiple emission sites of the nanostructures 18.

The nanostructures 18 are preferably disposed on an outer surface of second electrode 16, for example. The nanostructures 18, when energized, may emit electrons, if they themselves comprise electron emitting material 19. Alternatively, the energization preferably causes the nanostructured overcoating of electron emitting material 19 to emit electrons. The electrons may be accelerated from the cathode (e.g., second electrode 16) to the anode (e.g., first electrode 14), and may be received (stopped) by the anode to generate electromagnetic wave energy 23, such as but not limited to, x-rays, which may be monochromatic or polychromatic.

The transducer 10 may be fashioned in small dimensions suitable for insertion transcutaneously, into body cavities and into lumens. The transducer 10 may thus be used in imaging and/or radiation treatment in situ. Accordingly, imaging apparatus 24 may be provided to form images of structures illuminated by electromagnetic wave energy generated by transducer 10. Imaging apparatus 24 may comprise, without limitation, an energy emission detector, e.g., a film, a scintillating screen, a fluoroscope or a detector array. Another embodiment of a detector useful for imaging is described hereinbelow with reference to FIG. 3.

Reference is now made to FIG. 2, which illustrates an electromagnetic wave energy emitter 30, constructed and operative in accordance with another preferred embodiment of the present invention. Transducer 30 may include a probe that comprises a generally hollow cylindrical shell 32. In this embodiment, first and second electrodes 34 and 36, respectively, are preferably disposed and insulatingly spaced apart from one another on the cylindrical shell 32 by insulating gaps 38 on shell 32.

Reference is now made to FIG. 3, which illustrates an electromagnetic wave energy emitter 40, constructed and operative in accordance with yet another preferred embodiment of the present invention. In the embodiments of FIGS. 1 and 2, the emitter probe may be shaped as a slender needle. In the embodiment of FIG. 3, the emitter 40 preferably comprises a plurality of such needles, such as probes 41 and 42, which may be generally parallel to each other. Emitter 40 may form part of an imaging system, which cooperates with an energy emission detector 43, such as but not limited to, a linear coaxial array of detectors 44 disposed in a needle 45, which may have a geometric shape similar to that of probes 41 and 42. Detector 43 may be inserted generally in parallel to the energy transducer 40.

Probes 41 and 42 may be connected to individual energy sources 46 and 47, respectively. Alternatively, a single energy source may provide power to the probes 41 and 42. Detector 43 may be in communication with a processor 48, which may process the information or signals received from detector 43 to form images displayable on a display 49.

Figure 4:
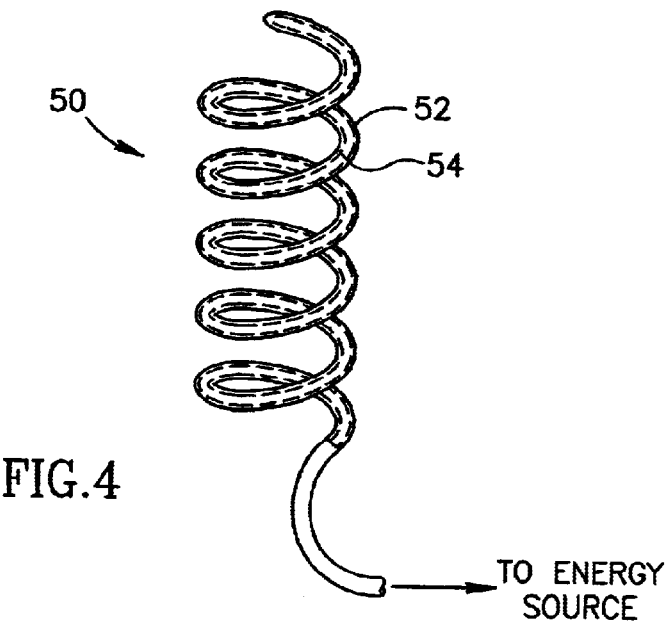
FIG. 4 is a simplified pictorial illustration of an electromagnetic wave energy emitter, constructed and operative in accordance with still another preferred embodiment of the present invention, having a helical construction.

Reference is now made to FIG. 4, which illustrates an electromagnetic wave energy emitter 50, constructed and operative in accordance with still another preferred embodiment of the present invention. In the previously described embodiments, the emitter probes may be shaped as slender needles. In the embodiment of FIG. 4, the emitter 50 and electrodes 52 and 54 may have a helical construction, which may increase the treatment volume. It is noted that the detector 46 of FIG. 3 may also be constructed with a helical construction.

It is noted that in the embodiments of FIGS. 2–4, a grid element (not shown) may be placed between the first and second electrodes to form a triode.

The electromagnetic wave energy emitters of the present invention may be used in a variety of medical procedures, such as but not limited to, vascular brachytherapy of coronary arteries (e.g., the femoral or carotid arteries), diagnosis and treatment of tumors of the pancreas, liver or gall bladder (e.g., via the bile ducts and pancreatic ducts), or the urinary bladder, rectum, colon, kidneys, prostate gland, or esophagus via other body passages and lumens. The type and level of the energy dosage (e.g., hard or soft x-rays) may depend on the type of tissue and treatment plan, for example.

The electromagnetic wave energy emitters of the present invention may also be used for non-medical applications, such as but not limited to, non-destructive evaluation of metals or other structural materials, imaging or detecting corrosion or blockages, or radiographic inspection of welds in pipes or other objects.

It will be appreciated by person skilled in the art that the present invention is not limited by what has been particularly shown and described herein above. Rather the scope of the present invention is defined by the claims that follow:

What is claimed is:

1. An electromagnetic wave energy emitter comprising:
a generally cylindrical probe comprising generally coaxial first and second electrodes, each of said electrodes having an at least partially cylindrical shape, one of said electrodes being energizable to emit electrons and the other of said electrodes being adapted to receive said electrons and generate electromagnetic wave energy; and
a grid element placed between said first and second electrodes.

2. The emitter according to claim 1 and further comprising a controller in communication with said grid element and adapted to control a potential of said grid element.

3. The emitter according to claim 1 wherein said grid element has an at least partially cylindrical shape.

4. The emitter according to claim 1 wherein said grid element is placed concentrically with respect to said first and second electrodes.

5. The emitter according to claim 1 wherein said grid element is placed non-concentrically with respect to said first and second electrodes.

6. The emitter according to claim 1 wherein said first electrode comprises a generally hollow cylindrical shell and said second electrode is disposed at least partially inside said first electrode.

7. The emitter according to claim 1 wherein said probe comprises a generally hollow cylindrical shell, and said first and second electrodes are disposed and insulatingly spaced apart from one another on said shell.

8. The emitter according to claim 1 wherein said first and second electrodes extend generally axially along a longitudinal length of said shell.

9. The emitter according to claim 1 and further comprising an energy source for energizing at least one of said first and second electrodes.

10. The emitter according to claim 1 and further comprising imaging apparatus adapted to form images of structures illuminated by electromagnetic wave energy generated by said emitter.

11. The emitter according to claim 1 wherein said first electrode comprises a cathode and said second electrode comprises an anode.

12. The emitter according to claim 1 wherein said first electrode comprises an anode and said second electrode comprises a cathode.

13. An electromagnetic wave energy emitter comprising:

a generally cylindrical probe comprising generally coaxial first and second electrodes, each of said electrodes having an at least partially cylindrical shape, one of said electrodes being energizable to emit electrons and the other of said electrodes being adapted to receive said electrons and generate electromagnetic wave energy; and nanostructures disposed on at least one of said first and second electrodes, said nanostructures being energizable to emit electrons.

14. The emitter according to claim 13 wherein said nanostructures comprise an electron emitting material.

15. The emitter according to claim 13 wherein said nanostructures comprise an overcoating of at least one nanolayer of an electron emitting material.

16. The emitter according to claim 15 wherein said electron emitting material has a surface morphology that is sufficiently nanoscopically rough to provide multiple potential field emission sites.

17. An electromagnetic wave energy emitter comprising:

a plurality of generally cylindrical probes, each probe comprising generally coaxial first and second electrodes, each of said electrodes having an at least partially cylindrical shape, one of said electrodes being energizable to emit electrons and the other of said electrodes being adapted to receive said electrons and generate electromagnetic wave energy, said probes being generally parallel to one other.

18. The emitter according to claim 17 and further comprising a grid element placed between said first and second electrodes.

19. An electromagnetic wave energy emitter comprising:

a generally cylindrical probe comprising generally coaxial first and second electrodes, each of said electrodes having an at least partially cylindrical shape, one of said electrodes being energizable to emit electrons and the other of said electrodes being adapted to receive said electrons and generate electromagnetic wave energy, wherein said probe has a generally helical construction.

20. The emitter according to claim 19 and further comprising a grid element placed between said first and second electrodes.

* * * * *